United States Patent
Choi et al.

(10) Patent No.: US 10,413,262 B2
(45) Date of Patent: Sep. 17, 2019

(54) MAMMOGRAPHY SYSTEM AND MAMMOGRAPHY PHOTOGRAPHING METHOD

(71) Applicants: Rayence Co., Ltd., Gyeonggi-do (KR); VATECH EWOO Holdings Co., Ltd., Gyeonggi-do (KR)

(72) Inventors: Sung Il Choi, Gyeonggi-do (KR); Woong Bae, Gyeonggi-do (KR); Tae Woo Kim, Gyeonggi-do (KR); Keun Yeong Kim, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 262 days.

(21) Appl. No.: 15/506,883

(22) PCT Filed: Aug. 27, 2015

(86) PCT No.: PCT/KR2015/008990
§ 371 (c)(1),
(2) Date: Feb. 27, 2017

(87) PCT Pub. No.: WO2016/032256
PCT Pub. Date: Mar. 3, 2016

(65) Prior Publication Data
US 2017/0281108 A1 Oct. 5, 2017

(30) Foreign Application Priority Data
Aug. 29, 2014 (KR) .......................... 10-2014-0114257

(51) Int. Cl.
*A61B 6/04* (2006.01)
*A61B 6/00* (2006.01)
(Continued)

(52) U.S. Cl.
CPC .............. *A61B 6/502* (2013.01); *A61B 6/025* (2013.01); *A61B 6/032* (2013.01); *A61B 6/0414* (2013.01);
(Continued)

(58) Field of Classification Search
CPC ....... A61B 6/025; A61B 6/032; A61B 6/0414; A61B 6/0435; A61B 6/4441; A61B 6/482;
(Continued)

(56) References Cited

U.S. PATENT DOCUMENTS 7,302,031 B2 * 11/2007 Hjarn ...................... A61B 6/02
378/23
2003/0194049 A1 10/2003 Claus et al.
(Continued)

FOREIGN PATENT DOCUMENTS

| JP | 2008-104673 A | 5/2008 |
| JP | 2010-187916 A | 9/2010 |
| KR | 10-2014-0087206 A | 7/2014 |

*Primary Examiner* — Irakli Kiknadze
(74) *Attorney, Agent, or Firm* — IP Legal Services, LLC

(57) ABSTRACT

Disclosed are a mammography system and a mammography imaging method that can prevent a subject from being exposed to radiation more than necessary by setting an optimum imaging condition according to a thickness of a subject's breast, and can obtain a high-quality medical image by setting an optimum FOV and correcting projection data according to the thickness of the breast. The mammography system includes: a mammography imaging device including a detector and an X-ray tube, and obtaining X-ray image data of a subject's breast from multiple angles; a thickness obtaining unit obtaining information on a thickness of the breast; and a rotation angle calculator calculating a rotation angle range of the X-ray tube, based on the information of the thickness of the breast, wherein the mammography imaging device obtains the X-ray image data
(Continued)

from multiple angles by performing radiography while rotating the X-ray tube within the rotation angle range.

7 Claims, 8 Drawing Sheets

(51) Int. Cl.
*A61B 6/03* (2006.01)
*A61B 6/02* (2006.01)

(52) U.S. Cl.
CPC .......... *A61B 6/0435* (2013.01); *A61B 6/4441* (2013.01); *A61B 6/5217* (2013.01); *A61B 6/5258* (2013.01); *A61B 6/544* (2013.01); *A61B 6/582* (2013.01); *A61B 6/583* (2013.01); *A61B 6/482* (2013.01)

(58) Field of Classification Search
CPC ..... A61B 6/502; A61B 6/5217; A61B 6/5258; A61B 6/544; A61B 6/582; A61B 6/583; A61B 6/12; A61B 6/464; A61B 6/481; A61B 6/102; A61B 6/4028; A61B 6/02; A61B 6/06; A61B 6/4291; A61B 6/037; A61B 6/04; A61B 6/4233
USPC ...................................................... 378/37, 62
See application file for complete search history.

(56) References Cited

U.S. PATENT DOCUMENTS

| | | |
|---|---|---|
| 2007/0098141 A1 | 5/2007 | Hjarn et al. |
| 2008/0101537 A1 | 5/2008 | Sendai |
| 2010/0208958 A1 | 8/2010 | Yamada et al. |
| 2014/0072100 A1* | 3/2014 | Jang ....................... A61B 6/022 378/37 |
| 2014/0185738 A1 | 7/2014 | Lee et al. |

* cited by examiner

MAMMOGRAPHY SYSTEM AND MAMMOGRAPHY PHOTOGRAPHING METHOD

CROSS REFERENCE TO RELATED APPLICATIONS

This application is a National Stage Patent Application of PCT International Patent Application No. PCT/KR2015/008990 (filed on Aug. 27, 2015) under 35 U.S.C. § 371, which claims priority to Korean Patent Application No. 10-2014-0114257 (filed on Aug. 29, 2014), the teachings of which are incorporated herein in their entireties by reference.

TECHNICAL FIELD

The present invention relates generally to a medical imaging system. More particularly, the present invention relates to a mammography system and a mammography imaging method.

BACKGROUND ART

Generally, a mammography system is an X-ray imaging system for early detection of breast cancer, and is configured to obtain a two-dimensional image by transmitting a predetermined dose of X-rays to a subject's breast, and detecting an amount of the transmitted X-rays by using an image sensor.

Recently, to overcome limitations of a conventional technology using a two-dimensional image for diagnosing breast cancer, digital breast tomosynthesis (DBT) is proposed, which uses a three-dimensional image to diagnose breast cancer.

DBT is a technology configured such that an X-ray tube is rotated within a limited range of an angle to obtain two-dimensional images from multiple angles, and the two-dimensional images are reconstructed to obtain a three-dimensional tomographic image.

A conventional mammography system applied with the DBT technology is configured such that a breast compression means is disposed between an X-ray source and an X-ray detector, and radiography is performed by the breast compression means compressing a breast in the state where the breast is placed at the upper portion of the X-ray detector.

Here, since a size of a breast and density of breast tissue vary from subject to subject, a thickness of a breast varies from subject to subject when the breast is compressed by the breast compression means for radiography, whereby a maximum angle allowing the X-ray tube to be rotated to obtain a DBT angle varies according to a thickness of a breast.

For example, as shown in FIG. 1, a thickness T of a breast in FIG. 1A is thicker than a thickness T' of a breast in FIG. 1B, whereby in order to image the entire breast with X-rays having a fixed X-ray irradiation angle, a rotation angle range of the X-ray tube in FIG. 1A is smaller than that of the X-ray tube in FIG. 1B.

However, the conventional mammography system is problematic in that since it has no means to adjust a rotation angle range of the X-ray tube according to a thickness of a breast, some subjects are exposed to radiation more than necessary.

The conventional mammography system is further problematic in that when a radiographed two-dimensional image is reconstructed to a three-dimensional image, the system may reconstruct the image including a non-subject area, whereby it may take longer to reconstruct.

DISCLOSURE

Technical Problem

The present invention has been made keeping in mind the above problems occurring in the related art.

Accordingly, the present invention is intended to propose a mammography system and a mammography imaging method, which is capable of imaging by setting an optimum imaging condition according to a thickness of a subject's breast, and is capable of correcting projection data and reconstructing an image by setting the thickness of the breast according to an optimum field of view (FOV).

The above and other objects and features of the invention will appear more fully hereinafter from a consideration of the following description. Further, it is understood that within the scope of the appended claims, the objects and features of the invention may be practiced.

Technical Solution

In order to achieve the above object, according to one aspect of the present invention, there is provided a mammography system including: a mammography imaging device including a detector and an X-ray tube, and being configured to obtain X-ray image data of a subject's breast from multiple angles; a thickness obtaining unit configured to obtain information on a thickness of the breast; and a rotation angle calculator configured to calculate a rotation angle range of the X-ray tube, based on the information of the thickness of the breast, wherein the mammography imaging device obtains the X-ray image data from multiple angles by performing radiography while rotating the X-ray tube within the rotation angle range.

In order to achieve the above object, according to another aspect of the present invention, there is provided a mammography imaging method, in which a detector and an X-ray tube that face each other with a subject's breast therebetween are used, the mammography imaging method including: obtaining information on a thickness of the breast; calculating a rotation angle range of the X-ray tube, based on the information on the thickness of the breast; and obtaining X-ray image data from multiple angles by performing radiography while rotating the X-ray tube within the rotation angle range.

Advantageous Effects

According to an embodiment of the present invention having the above-described characteristics, it is possible to prevent a subject from being exposed to radiation more than necessary by setting an optimum imaging condition according to a thickness of a subject's breast.

According to another embodiment of the present invention having the above-described characteristics, it is possible to obtain a high-quality medical image by setting an optimum field of view (FOV) and correcting projection data by using a compensation coefficient determined according to the thickness of the breast after radiography is performed by using a mammography system. Further, it is possible to reduce image reconstruction time by performing image reconstruction on the set FOV area.

MODE FOR INVENTION

The above and other related objects and features of the invention will be apparent from a reading of the following description of the disclosure found in the accompanying drawings. Therefore, those skilled in the art can easily understand the present invention. In the following description of the present invention, detailed descriptions of known functions and components incorporated herein will be omitted when it may make the subject matter of the present invention unclear. Reference will now be made in greater detail to an exemplary embodiment of the present invention, an example of which is illustrated in the accompanying drawings.

It will be further understood that the terms "comprises", "comprising", "includes", and/or "including" when used herein, specify the presence of stated features, integers, steps, operations, elements, and/or components, but do not preclude the presence or addition of one or more other features, integers, steps, operations, elements, components, and/or groups thereof.

Figure 1A:
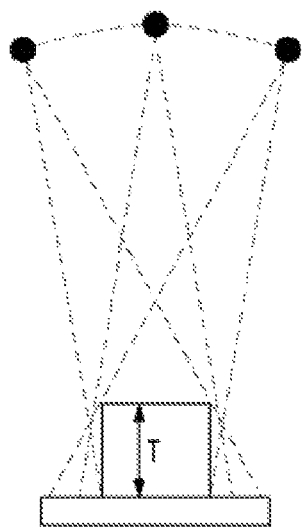
FIGS. 1A and 1B illustrates views of a rotation angle of an X-ray tube according to a thickness of a subject's breast.
Figure 1B:
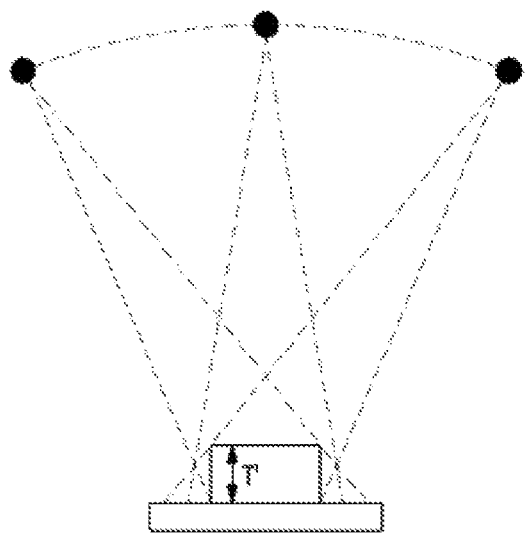
Figure 2:
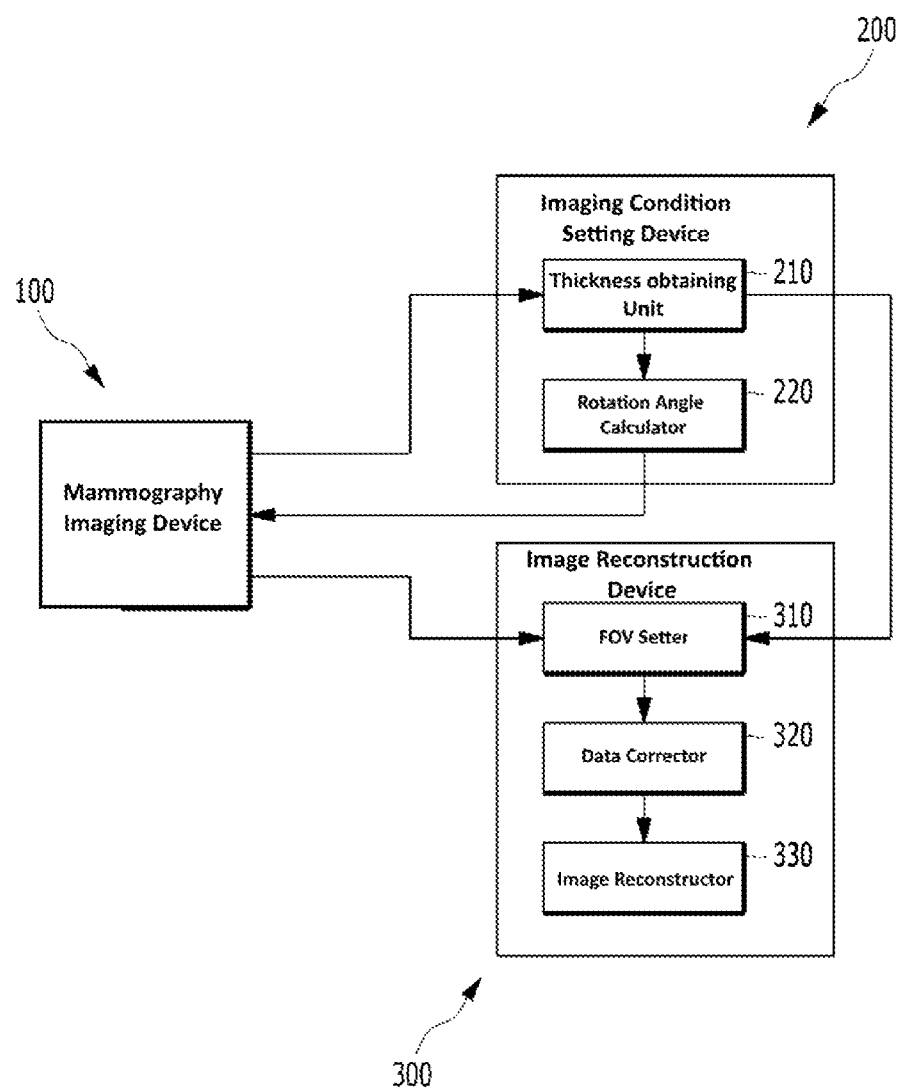
FIG. 2 illustrates a schematic diagram of a mammography system according to an embodiment of the present invention.
Figure 3:
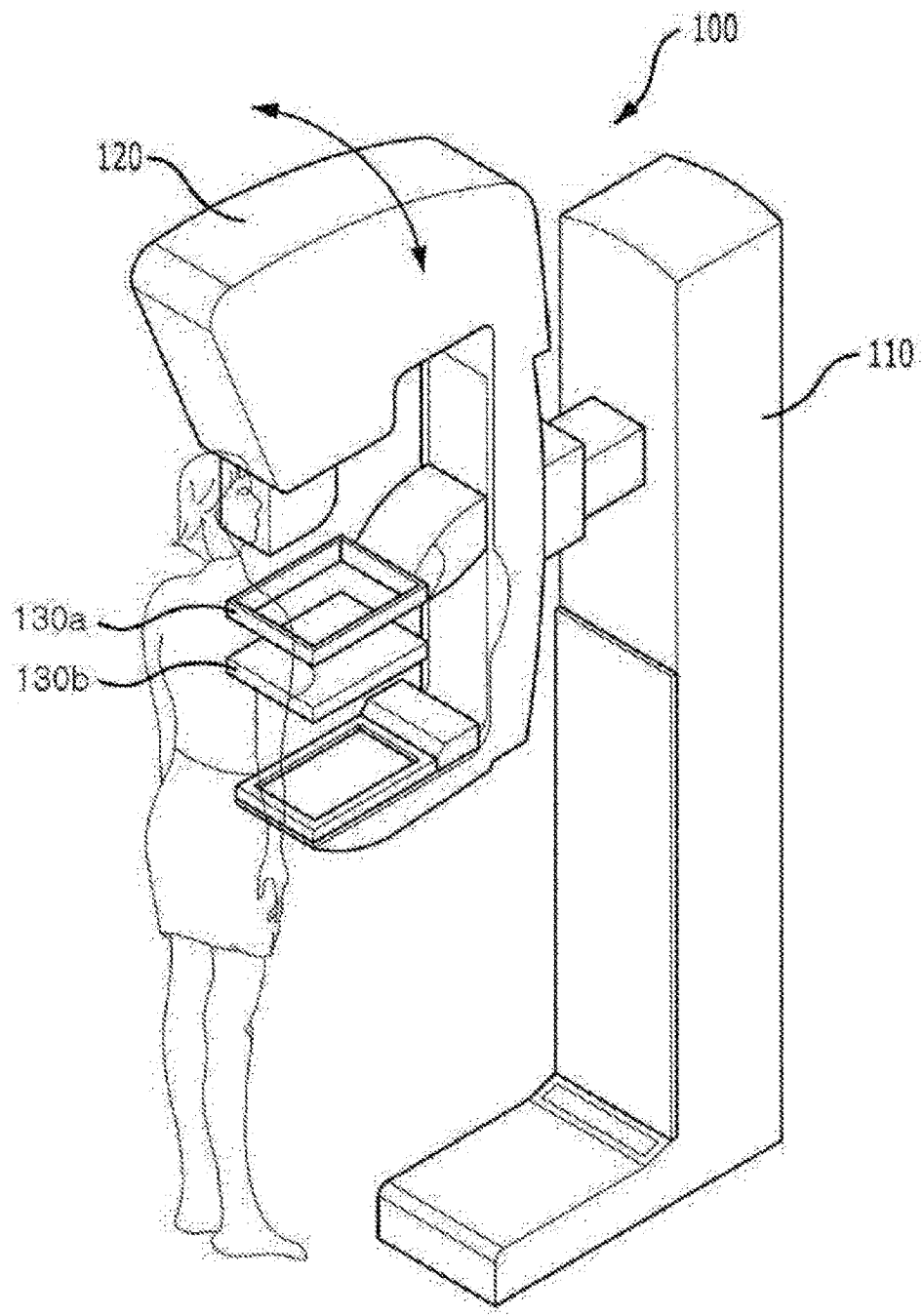
FIG. 3 illustrates a schematic view of a mammography imaging device according to an embodiment of the present invention.

FIG. 2 illustrates a schematic diagram of a mammography system according to an embodiment of the present invention; and FIG. 3 illustrates a schematic view of a mammography imaging device according to an embodiment of the present invention.

Referring to FIG. 2, a mammography system according to an embodiment of the present invention includes: a mammography imaging device 100; an imaging condition setting device 200; and an image reconstruction device 300.

For reference, the imaging condition setting device 200 and the image reconstruction device 300 may be integrally provided in the mammography imaging device 100, may be functionally included therein, or may be connected to the mammography imaging device 100 by wire or wirelessly. Further, in the description, various image data collectively refers to a set of information that can be displayed as an image through predetermined image processing. Accordingly, unless otherwise noted, the term "various images" also refers to "various image data" for realizing the images.

As shown in FIG. 3, the mammography imaging device 100 includes: a support 110; a gantry 120; a compression panel 130a; and a support panel 130b. Herein, an X-ray tube (not shown) may be provided inside the gantry 120; and an X-ray detector may be provided in the support panel 130b.

In an embodiment of the present invention, to obtain an image of digital breast tomosynthesis (DBT), in which a three-dimensional image is used to diagnose breast cancer, in the state where a subject's breast is placed at an upper portion of the support panel 130b, the compression panel 130a holds the breast by compressing it, and then radiography is performed while the gantry 120 or the X-ray tube is rotated by a predetermined angle range.

Further, the imaging condition setting device 200 includes: a thickness obtaining unit 210 configured to obtain information on a thickness of the subject's breast; a rotation angle calculator 220 configured to calculate a rotation angle range of the X-ray tube of the mammography imaging device 100, based on the information of the thickness of the breast.

Reference will be made in detail to the thickness obtaining unit 210 and the rotation angle calculator 220, hereinbelow.

Firstly, the thickness obtaining unit 210 is configured to transmit the information on the thickness of the subject's breast to the rotation angle calculator 200 and a FOV setter 310 of the image reconstruction device 300 by obtaining information on a thickness of a subject's breast from the mammography imaging device 100.

Herein, the thickness obtaining unit 210 may include a distance measuring sensor (not shown) that is provided in at least one of the compression panel 130a and the support panel 130b of the mammography imaging device 100, wherein the distance measuring sensor measures a distance between the compression panel 130a and the support panel 130b, whereby it is possible to obtain the information on the thickness of the subject's breast. For reference, as the distance measuring sensor, an infrared sensor, a ultrasonic sensor, or a laser sensor can be used.

Further, the thickness obtaining unit 210 may obtain the information on the thickness of the subject's breast by detecting the number of rotations of a gear wheel (not shown) that is provided in the support supporting the compression panel 130a and the support panel 130b, and is rotated to adjust a height of the compression panel 130a.

Next, the rotation angle calculator 220 calculates the rotation angle range of the X-ray tube of the mammography imaging device 100, based on the information on the thickness of the subject's breast received from the thickness obtaining unit 210. Herein, an equation for calculating the rotation angle range is as follows.

Figure 4:
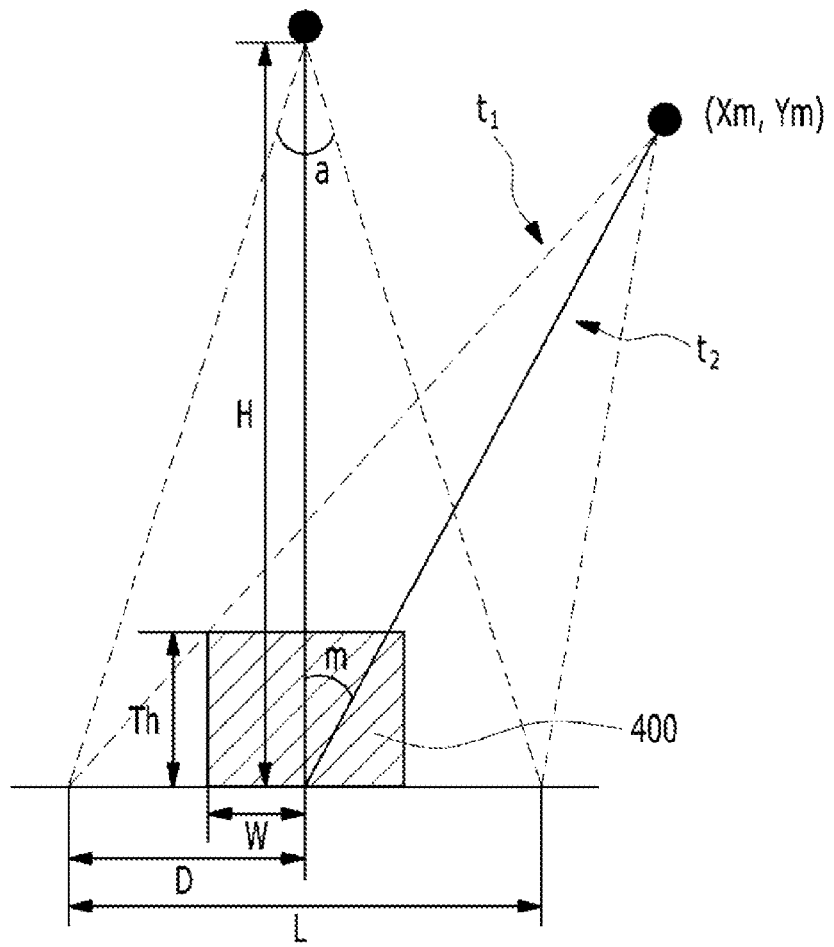
FIG. 4 illustrates a view of a method of calculating the rotation angle of the X-ray tube according to an embodiment of the present invention.

FIG. 4 illustrates a view of a method of calculating the rotation angle of the X-ray tube according to an embodiment of the present invention.

Referring to FIG. 4, a half value D of a width L of the X-rays emitted from the X-ray tube, that is, a length L of an X-ray irradiation field in an X-axis may be obtained through [Equation 1].

$$\tan\left(\frac{a}{2}\right) = \frac{D}{H} \qquad \text{[Equation 1]}$$

Herein, an X-ray irradiation angle a of X-rays, and a distance H from the X-ray tube to the support panel 130b, that is, to the X-ray detector are constants predetermined according to characteristics and specifications of the mammography imaging device 100.

Further, at position coordinates (Xm, Ym) of the X-ray tube at a maximum rotation angle m corresponding to the information on the thickness of the breast, of the two line segments representing the X-ray irradiation field of the X-ray tube, an equation of the left line segment t1 that is in contact with the subject, that is, a breast area 400 may be expressed as [Equation 2].

$$Y = \left(\frac{Th}{D-W}\right)(X+D) \quad \text{[Equation 2]}$$

Herein, a value Th of the thickness of the breast is a value obtained through the thickness obtaining unit 210, and a half value W of the breast width is a predetermined constant, wherein the value W may be set as a half value of an average width of women's breasts.

In [Equation 2], when a slope value is replaced with K, and then the position coordinates (Xm, Ym) of the X-ray tube at the maximum rotation angle m corresponding to the thickness of the breast are substituted, it may be expressed as [Equation 3].

$$Y_m = KX_m + KD \quad \text{[Equation 3]}$$

Further, an expression of a length H of a line segment t2, which connects the position coordinates (Xm, Ym) of the X-ray tube at the maximum rotation angle m corresponding to the information on the thickness of the breast, and the origin, may be expressed as [equation 4].

$$X_m^2 + Y_m^2 = H^2 \quad \text{[Equation 4]}$$

Herein, as described above, the distance H from the X-ray tube to the X-ray detector is a constant predetermined according to characteristics and specifications of the mammography imaging device 100.

When [Equation 3] and [Equation 4] are calculated together, values of the position coordinates (Xm, Ym) of the X-ray tube at the maximum rotation angle m corresponding to the information on the thickness of the breast may be obtained, and the maximum rotation angle m may be obtained through [Equation 5].

$$\tan(m) = \frac{X_m}{Y_m} \quad \text{[Equation 5]}$$

In other words, the rotation angle range of the X-ray tube of the mammography imaging device 100, which is calculated based on the information on the thickness of the breast received from the thickness obtaining unit 210, is determined from −m° to m°.

Herein, the thicker the thickness of the breast is, the rotation angle range calculated through [Equation 1] to [Equation 5] is smaller, and on the contrary, the thinner the thickness of the breast is, the rotation angle range is larger.

The mammography imaging device 100 may obtain X-ray image data from multiple angles by performing radiography while rotating the X-ray tube within the calculated rotation angle range, whereby it is possible to prevent a subject from being exposed to radiation more than necessary.

Meanwhile, the rotation angle calculator 220 may be configured to calculate and output the rotation angle range through [Equation 1] to [Equation 5] whenever the information on the thickness of the subject's breast is obtained, or may be configured to output the rotation angle range predetermined according to the obtained thickness of the breast when the thickness obtaining unit 210 obtains the information on the thickness of the breast.

Further, the imaging condition setting device 200 may additionally set a tube voltage kVp and a dose mAs of the mammography imaging device 100 according to the information on the thickness of the breast. For example, after information on a tube voltage and a dose according to recommended standards by a thickness of a breast is made in the form of a table, a tube voltage, and a dose in the table, which corresponds to the information on the obtained thickness of the breast, may be selected, whereby it is possible to set the tube voltage and the dose. Further, the imaging condition setting device 200 may set the tube voltage and the dose using auto exposure control (AEC) as a publicly known art, that is, a technology that is capable of setting a tube voltage and a dose of a main-shot according to a thickness of a breast through a pre-shot.

Next, reference will be made in detail to the image reconstruction device 300, hereinbelow.

The image reconstruction device 300 includes: a FOV setter 310 configured to set a field of view (FOV) corresponding to a size of the subject's breast by receiving X-ray image data from multiple angles radiographed from the mammography imaging device 100, that is, projection data from multiple angles, and the information on the thickness of the subject's breast from the thickness obtaining unit 210; a data corrector 320 configured to correct the projection data by receiving the projection data, and the set FOV information from the FOV setter 310; and an image reconstructor 330 configured to reconstruct the data into a three-dimensional tomographic image by receiving the corrected projection data and the set FOV information from the data corrector 320.

Reference will be made in detail to the FOV setter 310, the data corrector 320, and the image reconstructor 330, hereinbelow.

Figure 5A:
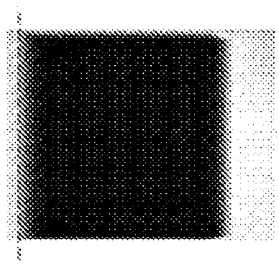
FIGS. 5A to 5C illustrates views of a method of setting a field of view (FOV) according to an embodiment of the present invention.
Figure 5B:
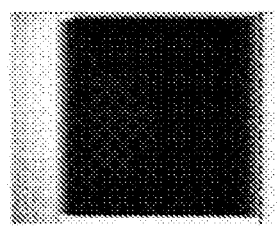
Figure 5C:
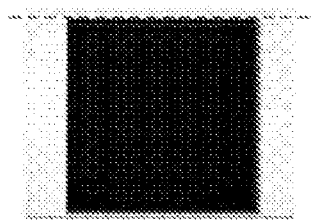

FIG. 5 illustrates views of a method of setting a FOV according to an embodiment of the present invention, wherein FIG. 5A is a view showing detection of the left border of the subject; FIG. 5B is a view showing detection of the right border thereof; and FIG. 5C is a view showing detection of the upper border thereof.

Firstly, the FOV setter 310 receives the projection data from multiple angles radiographed by the mammography imaging device 100, and then detects right, left, upper, and lower borders of the subject, namely, the subject's breast by using an X-ray image from multiple angles based on the received X-ray image data from multiple angles, thereby determining coordinates of X-axis and Y-axis of the FOV, and lengths thereof. Here, the lower border may be a lower end of the X-ray detector, so the coordinates of X-axis and Y-axis of the FOV, and the lengths thereof may be determined by detecting the right, left, and upper borders.

Further, the FOV setter 310 receives the information of the thickness of the breast from the thickness obtaining unit 210 of the imaging condition setting device 200, and sets the information as a length of Z-axis. In other words, the area of the FOV set by the FOV setter 310 is in a three-dimensional rectangular parallelepiped shape.

The FOV setter 310 transmits information on the set FOV and the projection data from multiple angles received from the mammography imaging device 100, to the data corrector 320.

Figure 6:
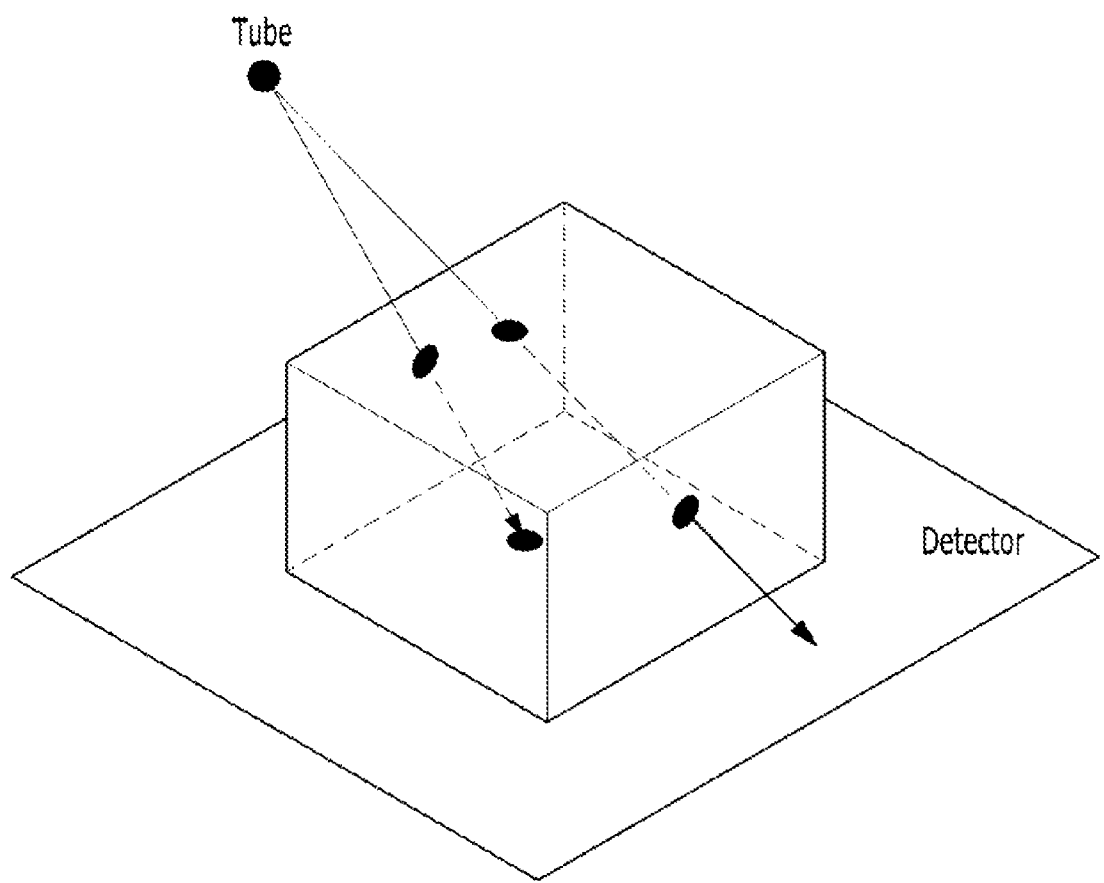
FIG. 6 illustrates a view of a path length of X-rays through the subject from the mammography imaging device according to an embodiment of the present invention.
Figure 7A:
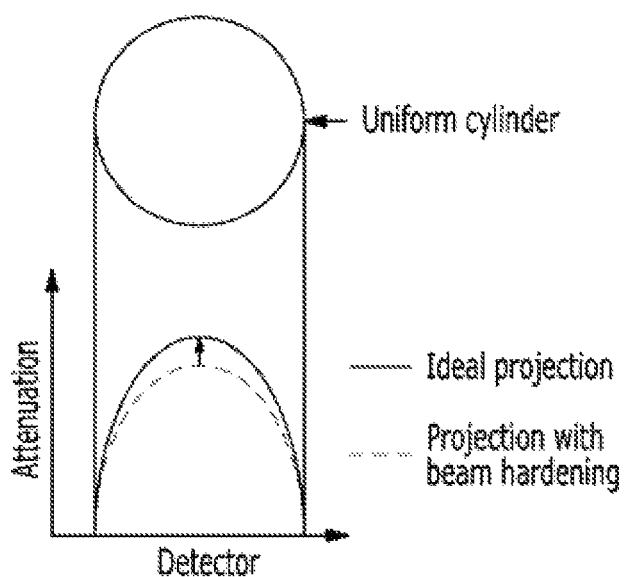
FIGS. 7A and 7B illustrates views of energy attenuation of X-rays through the subject from the mammography imaging device according to an embodiment of the present invention.
Figure 7B:
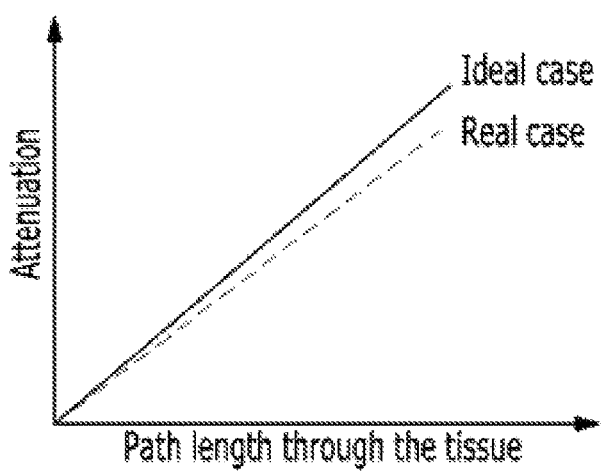

FIG. 6 illustrates a view of a path length of X-rays through the subject from the mammography imaging device according to an embodiment of the present invention; and FIG. 7 illustrates views of energy attenuation of X-rays through the subject from the mammography imaging device according to an embodiment of the present invention.

Referring to FIG. 6, the data corrector 320 firstly receives the information on the set FOV from the FOV setter 310, and calculates a path length of X-rays emitted from the X-ray tube through the set FOV area, that is, the subject area, by each rotation angle of the X-ray tube.

In other words, the path length of X-rays through the FOV area (that is, an X-ray transmission length), as shown in FIG. 6, is identified by calculating a length of a line segment that connects of dots on two surfaces, which a vector connecting the X-ray tube and a pixel of the X-ray detector meets while penetrating through the set FOV area.

Then, of compensation coefficients in a predetermined compensation table, a compensation coefficient corresponding to the X-ray transmission length, and a predetermined X-ray energy keV is reflected in an amount value of X-ray attenuation measured in the pixel of the projection data, and thereby the amount of X-ray attenuation is compensated, whereby it is possible to correct the projection data.

Herein, the compensation table may be set through a preliminary experiment, wherein the experiment is conducted by radiographing an anthropomorphic phantom having tissue and shape similar to a human breast. More specific process is as follows.

Firstly, based on the amount of X-ray attenuation measured by radiographing the anthropomorphic phantom, an acquisition value table is made. Herein, the acquisition value table may be in the form of an index of the X-ray energy keV and the path length of X-rays through the anthropomorphic phantom (that is, the X-ray transmission length).

Then, the compensation coefficients in the compensation table are determined by calculating a ratio relationship between each value in the acquisition value table and a corresponding theoretical value. Herein, the theoretical value is an ideal value, that is, an ideal amount value of X-ray attenuation, which can be obtained according to the X-ray energy keV and the X-ray transmission length when the anthropomorphic phantom is radiographed, and those skilled in the art can easily understand that the theoretical value can be calculated through X-ray attenuation principles, etc.

In other words, the compensation table is created with the X-ray energy keV and the X-ray transmission length as an index; and a compensation coefficient in the compensation table, which corresponds to the X-ray energy keV and the X-ray transmission length of the acquisition value, is reflected to an acquisition value, whereby a relationship for calculating the theoretical value is established.

Referring to FIG. 7, as a result of measuring the amount of X-ray attenuation through the anthropomorphic phantom, it may be understood that an actual acquired value is attenuated less than the theoretical value, and particularly, the longer the path length of X-rays through the subject is, the bigger the difference in the amount of X-ray attenuation between the acquisition value and the theoretical value is. This is because of beam hardening phenomenon, etc., wherein the beam hardening phenomenon is a cause of image deterioration, such as a case where an artifact occurs on the obtained X-ray image.

In an embodiment of the present invention, by using the above described compensation table, the acquisition value is compensated such that the acquisition value is corrected to have the same value as the theoretical value, whereby it is possible to obtain high-quality projection data.

The data corrector 320 transmits the corrected projection data obtained through the above described data correction process, and the FOV information set by the FOV setter 310, to the image reconstructor 330.

The image reconstructor 330 produces three-dimensional tomographic image data by performing image reconstruction on the received projection data. Here, the image reconstructor 330 performs image reconstruction on the set FOV area, whereby it is possible to reduce image reconstruction time.

Figure 8:
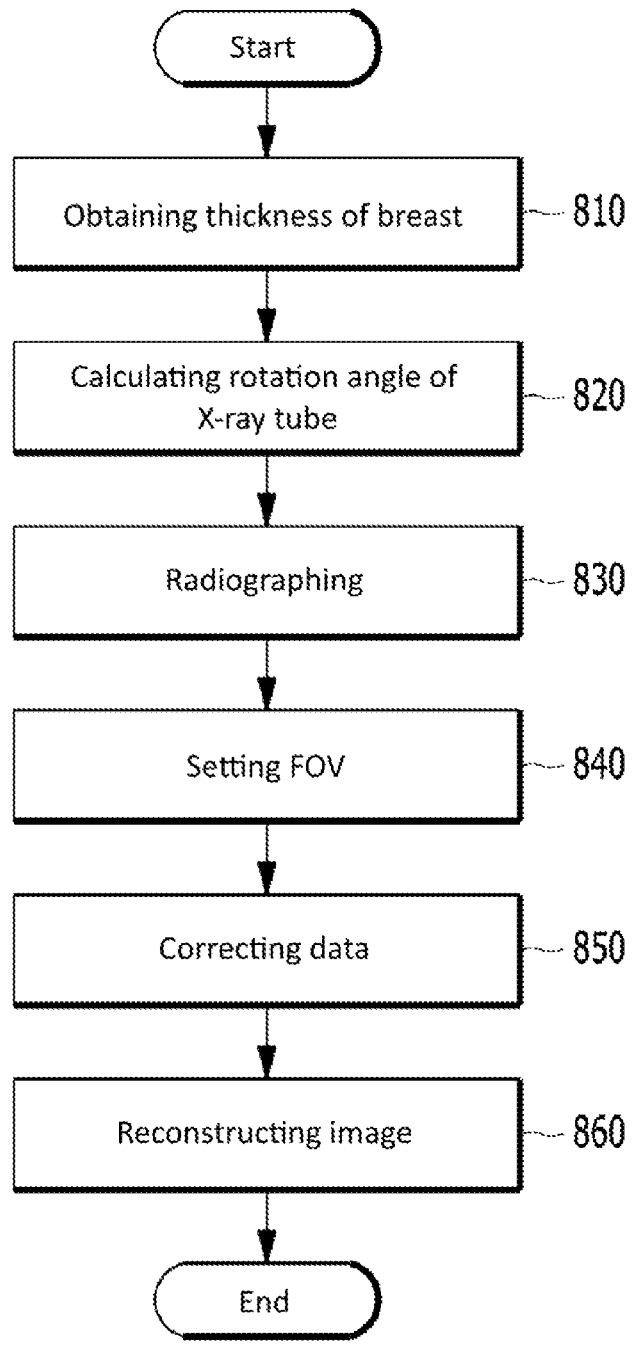
FIG. 8 illustrates a flow chart of the mammography imaging device according to an embodiment of the present invention.

FIG. 8 illustrates a flow chart of the mammography imaging device according to an embodiment of the present invention, and the specific description of the embodiment is the same as in the above description, so operation procedure thereof will be described, hereinbelow.

Firstly, the thickness obtaining unit 210 obtains the information on the thickness of the subject's breast (810).

Herein, the thickness obtaining unit 210 may be configured such that the distance measuring sensor that is provided in at least one of the compression panel 130a and the support panel 130b of the mammography imaging device 100 measures a distance between the compression panel 130a and the support panel 130b, whereby the information on the thickness of the subject's breast is obtained.

Further, the thickness obtaining unit 210 may obtain the information on the thickness of the breast by detecting the number of rotations of the gear wheel that is provided in the support supporting the compression panel 130a and the support panel 130b, and is rotated to adjust a height of the compression panel 130a.

Then, the rotation angle calculator 220 calculates the rotation angle range of the X-ray tube of the mammography imaging device 100 through [Equation 1] to [Equation 5], based on the information on the thickness of the subject's breast received from the thickness obtaining unit 210 (820), and transmits the rotation angle range to the mammography imaging device 100.

Herein, the thicker the thickness of the breast is, the rotation angle range calculated through [Equation 1] to [Equation 5] is smaller, and on the contrary, the thinner the thickness of the breast is, the rotation angle range is larger.

Meanwhile, the rotation angle calculator 220 may be configured to calculate and output the rotation angle range through [Equation 1] to [Equation 5] whenever the information on the thickness of the subject's breast is obtained, or may be configured to output the rotation angle range predetermined according to the obtained thickness of the breast when the thickness obtaining unit 210 obtains the information on the thickness of the breast.

The mammography imaging device 100 radiographs the subject while rotating the X-ray tube within the received rotation angle range (830), and transmits the radiographed projection data to the FOV setter 310 of the image reconstruction device 300.

Firstly, the FOV setter 310 receives the radiographed projection data from the mammography imaging device 100, and then detects the right, left, upper, and lower borders of the subject, namely, the subject's breast based on the projection data, thereby determining coordinates of X-axis and Y-axis of the FOV, and lengths thereof, and receives the information of the thickness of the breast from the thickness obtaining unit 210, thereby setting the information as a length of Z-axis (840).

Then, the data corrector 320 calculates the path length of X-rays emitted from the X-ray tube through the FOV, that is, the subject area by receiving the projection data, and the set FOV information from the FOV setter 310, and then of the compensation coefficients in the predetermined compensation table, a compensation coefficient corresponding to the X-ray transmission length and a predetermined X-ray energy keV is reflected in an amount value of X-ray attenuation measured in the pixel of the projection data to compensate the amount of X-ray attenuation, whereby the projection data is corrected (850).

Then, the data corrector 320 transmits the set FOV information and the corrected projection data, to the image reconstructor 330.

The image reconstructor 330 produces three-dimensional tomographic image data by performing image reconstruction on the received projection data (860). Here, the image reconstructor 330 performs image reconstruction on the set FOV area, whereby it is possible to reduce image reconstruction time.

While the described embodiment represents the preferred form of the present invention, it is to be understood that modifications will be apparent to those skilled in that art without departing from the spirit of the invention.

The scope of the invention is therefore to be determined solely by the appended claims.

The invention claimed is:

1. A mammography system comprising:
a mammography imaging device including a detector and an X-ray tube, and configured to obtain X-ray image data of a subject's breast from multiple angles;
a thickness obtaining unit configured to obtain information on a thickness of the breast;
a rotation angle calculator configured to calculate a rotation angle range of the X-ray tube, based on the information of the thickness of the breast;
a FOV setter configured to set a field of view (FOV) corresponding to a size of the breast, based on the information of the thickness of the breast and the X-ray image data from multiple angles; and
an image reconstructor configured to reconstruct a three-dimensional tomographic image data of the FOV, based on the X-ray image data from multiple angles,
wherein the mammography imaging device obtains the X-ray image data from multiple angles by performing radiography while rotating the X-ray tube within the rotation angle range, and,
wherein the FOV setter is configured to detect a border of the breast from the X-ray image data from multiple angles, and sets the FOV based on both the border of the breast and the thickness of the breast.

2. The mammography system of claim 1, wherein the mammography imaging device further includes a compression panel configured to compress the breast between the X-ray tube and the detector and a support panel, and
the thickness obtaining unit is configured to obtain the information of the thickness of the breast, based on a distance between the compression panel and the support panel.

3. The mammography system of claim 2, wherein the support panel is the detector.

4. The mammography system of claim 1, wherein the mammography imaging device is further configured to set a tube voltage and a dose corresponding to the information on the thickness of the breast.

5. The mammography system of claim 1, further comprising: a data corrector configured to correct the X-ray image data from multiple angles by calculating a value of X-ray attenuation corresponding to a transmission length through the FOV at the multiple angles of the X-ray tube,
wherein the image reconstructor is configured to produce the three-dimensional tomographic image data of the FOV, based on the corrected X-ray image data from multiple angles.

6. The mammography system of claim 5, wherein the data corrector corrects the X-ray image data from multiple angles using a compensation coefficient corresponding to the X-ray transmission length.

7. The mammography system of claim 6, wherein the data corrector corrects the X-ray image data from multiple angles using a predetermined compensation table.

* * * * *